United States Patent [19]
Monroe

[11] 3,949,738
[45] Apr. 13, 1976

[54] PEAK VENTILATORY FLOW INDICATOR

[75] Inventor: Robert Grier Monroe, Westwood, Mass.

[73] Assignee: Thermo Electron Corporation, Waltham, Mass.

[22] Filed: Nov. 1, 1974

[21] Appl. No.: 520,189

[52] U.S. Cl. ............................ 128/2.08; 116/117 R
[51] Int. Cl.² ............................................ A61B 5/08
[58] Field of Search ................... 128/2.08, DIG. 29; 272/57 F; 116/117 R, 112, 114 AM, 114 R; 73/194 R, 388 R, 396, 207, 208, 302; 46/44; 340/240; 220/89 A

[56] References Cited
UNITED STATES PATENTS

| | | | |
|---|---|---|---|
| 737,008 | 8/1903 | Nichol | 272/57 F |
| 741,492 | 10/1903 | Henrichsen | 128/2.08 |

OTHER PUBLICATIONS

Bono, E. F. De, A Whistle for Testing Lung Function, The Lancet, Vol. 2 (63) No. 7318, Nov. 30, 1963, pp. 1146 & 1147.

Primary Examiner—S. Clement Swisher
Assistant Examiner—Denis E. Corr
Attorney, Agent, or Firm—James L. Neal

[57] ABSTRACT

A peak ventilatory flow rate indicator includes a hollow tube open at each end and has a series of small graded openings which hold a liquid by surface tension. When a subject ventilates his lungs through the tube as rapidly as possible, the number of graded openings from which the liquid is expelled is a function of peak ventilatory flow rate and an indication of pulmonary function.

12 Claims, 6 Drawing Figures

U.S. Patent   April 13, 1976   3,949,738
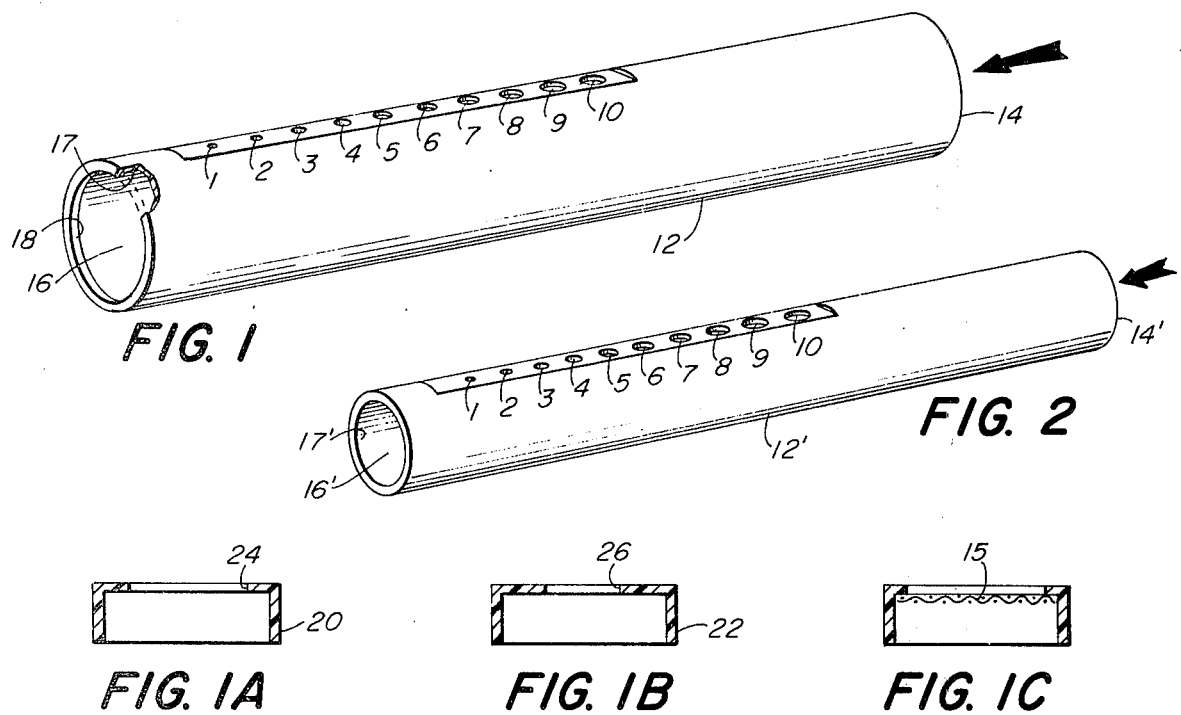
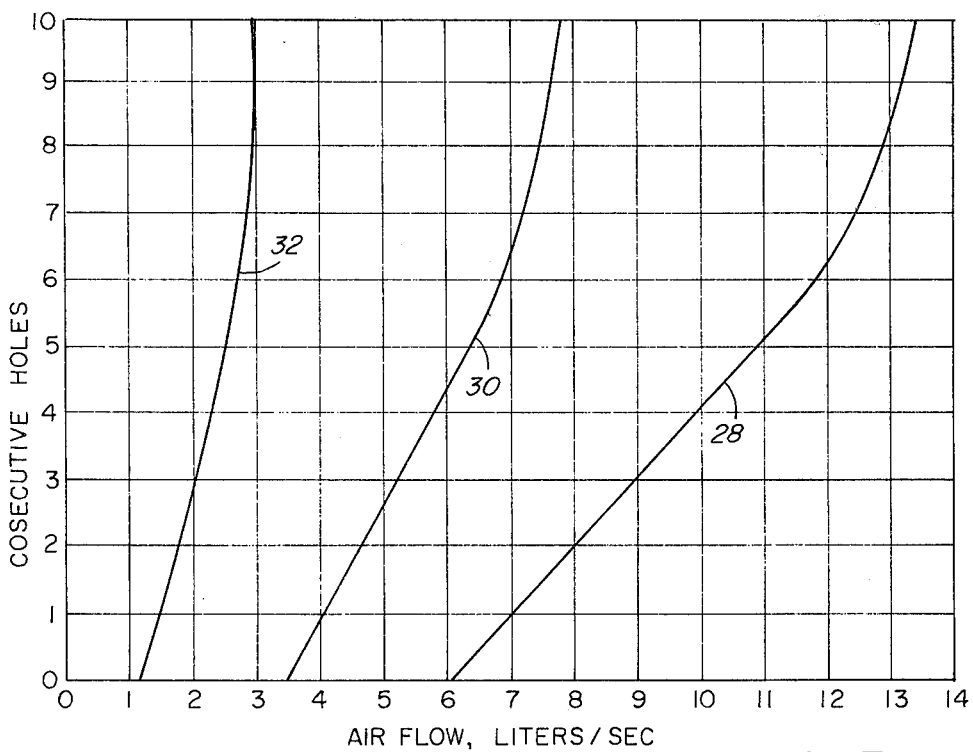

PEAK VENTILATORY FLOW INDICATOR

BACKGROUND OF THE INVENTION

The present invention relates to an indicator useful in testing the pulmonary function of a subject. The peak ventilatory flow rate of a subject is a good indication of overall pulmonary function. Peak expiratory flow rate is a widely recognized indication of pulmonary function with reference to certain lung conditions, such as asthma and emphysema. Persons not afflicted with such lung conditions can expel the air from the lungs much more rapidly than persons who are afflicted. Numerous devices for measuring the expiratory flow rate are provided. These devices are frequently expensive and complex.

SUMMARY OF THE INVENTION

The present invention involves a highly simplified instrument for measuring peak ventilatory flow rate to thus provide a measure of overall pulmonary function. The instrument may consist of a single unitary member having no moving parts. It may also be used with very simple adapters which extend its range of operation.

Briefly, the instrument comprises an elongated hollow tube forming a slight resistance to the passage of air and having along its walls a series of openings graded as to size. The openings are sized so that they may retain a meniscus of water or other suitable liquid by surface tension and so that they may be visually observed to determine whether or not a meniscus of liquid is present. An indication of pulmonary function is provided by having a subject ventilate as rapidly as possible through the open tube. The resistance to the passage of air creates a slight pressure drop across the tube so there is a tendency for the air to pass through the series of graded openings thus expelling the meniscus of liquid therein. The indication of pulmonary function is provided by the number and size of the graded openings from which the meniscus is expelled. The larger meniscus is the one most readily expelled and succeeding smaller ones become succeedingly more difficult. Therefore, the peak ventilatory flow of the subject is related to the number of the graded openings from which the meniscus of fluid is expelled.

BRIEF DESCRIPTION OF THE DRAWINGS

FIG. 1 is a perspective view showing preferred embodiment of the invention;

FIGS. 1A, 1B and 1C show attachments for the apparatus of FIG. 1;

FIG. 2 shows an alternate embodiment of the invention; and

FIG. 3 is a graphical showing of the relationship of peak expiratory flow and the number of holes from which liquid is discharged when the apparatus of FIG. 1 is used.

DETAILED DESCRIPTION OF THE INVENTION

Referring to FIG. 1, there is shown an elongated tubular member 12 having a fully open end 14 and an end 17 forming an opening 16 adjacent to which an inwardly projecting annular flange 18 forms a constriction. The flange 18 extends inward for a small distance relative to the overall radius of the tubular member 12 but a sufficient amount to create a small pressure drop across member walls when air is forced through the member from the end 14. That is, the resistance to passage of air provided by the flange 18 needs to be readily perceptible but may otherwise be small. The fully open end 14 serves as a mouthpiece. Anatomical shaping of the mouthpiece is not essential but may be provided as desired. The tubular member is sized so that resistance to flow of air therethrough is negligible, except for the effect of the flange 18. Further, it is shown in convenient circular cross section but oval and other cross-sectional configurations are useable. As used in this application, "tubular member" is not to be limited to devices of circular cross sections.

Distributed along the wall of the tubular member 12, between the mouthpiece 14 and the annular flange 18, is a series of graded apertures numbered 1 through 10 in ascending order of size. Each aperture is sufficiently small that it will hold a selected liquid, for example water, by surface tension and sufficiently large that the presence or absence of liquid in the aperture may be readily observed.

In operation, the apertures 1 – 10 may be filled with water which is held in place by its surface tension. The water is applied to the apertures in any convenient manner, as by dipping the tubular member into a vessel of water or by holding it under a running faucet. A subject is directed to take a deep breath and expel all of the air through the tubular member 12 as rapidly as possible. The resistance to the passage of air through the tube, produced primarily by the annular projection 18, creates within the tubular member a pressure higher than the outside pressure. This tends to force air through the apertures 1 – 10, thus expelling the water therefrom. Aperture 10 is the aperture from which water is most easily expelled and thereafter water is expelled from the other apertures in order of size, depending upon the magnitude of the pressure drop. It will be apparent that a relatively great pressure drop across the tube is required to expel water from the smaller apertures. Since the pressure drop is related to the peak explitory flow rate from the subject, the pulmonary function of the subject can be evaluated in relation to the number of apertures from which the water is expelled.

The operation can be reversed to determine the power of subject to inhale simply by directing the subject to exhale completely and then inhale as rapidly as possible through the tubular member. In this circumstance, water is expelled from the apertures into the tubular member by a relatively lower pressure therein.

In the preferred embodiment, the series of graded apertures 1 – 10 are arranged along the tubular member 12 in a line parallel to its longitudinal axis, with the largest opening adjacent the mouthpiece and the others in descending order of size toward the opposite end 17 of the tubular member. However, the applicant does not view its invention as limited to this arrangement of apertures or to ten apertures. Various arrangements and numbers of apertures are useable. The number and arrangement shown in FIG. 1 has been found to permit a quick and easy reading of the instrument. Further, while the annular projection 18 is a preferred method of resisting the flow of air through the tubular member 12, other resistance can be used. For example, as shown in FIG. 1C, a screen 15 could extend at least partially across the end of the member 12. As shown in the drawing, the screen 15 is mounted in an adapter 19 which fits over end 17 of member 12. Also, as shown in FIG. 2, the tubular member could be of sufficiently small cross sectional area to create a substantial resistance to the passage of air during use by the subject.

It should be noted that the annular constriction or a screen constriction may produce substantially all of the resistance at its locus so that the section of the tubular member 12 between the mouthpiece 14 and the constriction is characterized by substantially uniform pressure. On the other hand, when resistance to air flow is produced by a relatively small tube, there will be a pressure gradient created along the tube, a relatively high pressure being generated near the mouthpiece 14 and decreasing along the length of the tubular member 12 to zero at its opposite end 17. A tubular member characterized by such a pressure gradient would require that the apertures 1 – 10 in its wall be calibrated in size to take the variation in pressure into consideration. For example, the increment of change in size of adjacent apertures would be smaller. In any case, the apertures could be grouped within a small area of the tubular member 12 or distributed radially around the tube.

Referring now to FIGS. 1A and 1B, there are shown adapters 20 and 22 having openings 24 and 26, respectively. The opening 24 is smaller than the opening 16 and the opening 26 is smaller than the opening 24. Either of these adapters may be placed over the end 17 of the tubular member 12 to provide a constriction smaller than that provided by the flange 18. The smaller the opening provided at the end of the tubular member 12, the larger will be the pressure drop; correspondingly, the greater will be the number of apertures from which water will be discharged for a given peak ventilatory flow rate. The overall operation of the device and the function of the adapters 20 and 22 can be better understood by reference to FIG. 3.

FIG. 3 is a plot of the number of holes from which fluid is discharged versus the average liter per second peak expiratory flow. Three curves appear. Curve 28 corresponds to the opening provided by the flange 18. The curve 30 corresponds to the opening 24 in adapter 20 and the curve 32 corresponds to the opening 26 in the adapter 22. The various sized openings correspond to the anticipated peak ventilatory flow of various subjects. For example, small children will have a smaller peak ventilatory flow than an adult. For this reason, the ability to read the pulmonary condition of a small child may be enhanced by utilizing a smaller opening in the end 17 of the tubular member 12 than that used for an adult.

The curves shown in FIG. 3 are plotted from empirical results and are given by way of example to illustrate the kinds of curves and results that can be expected and are not intended to apply to all embodiments or configurations of the apparatus which might be produced according to this invention. The structure producing the results shown in FIG. 3 consists of a 6 inch long hollow tube having a circular cross sectional configuration and a ⅞ inch internal diameter. The walls of the tubular member are 1/16 inch thick and constructed of a clear thermoplastic material. The opening formed by the flange 18 is 0.83 inches in diameter and the openings 24 and 26 are 0.77 inches in diameter and 0.53 inches in diameter, respectively. The apertures 1 through 10 are positioned along the tube substantially as shown in FIG. 1 and range in fairly evenly graded sizes from approximately 0.173 inches in diameter to 0.055 inches in diameter.

Since certain changes may be made in the above construction without departing from the scope of the invention, it is intended that all matter contained in the above description or shown in the drawings be interpreted as illustrative and not in a limiting sense.

I claim:

1. A peak ventilatory flow rate indicator comprising an elongated tubular member having both ends open, one end serving as a mouthpiece, said member being constricted to resist air flow therethrough when air is discharged into said mouthpiece thereby to produce across the wall of said member a pressure drop having magnitude functionally related to ventilatory flow rate, and a series of openings through the wall of said member for retaining thereacross a meniscus of a selected liquid, each of said openings being of a size predetermined so that such meniscus thereacross is dislodged by a pressure drop across the wall of said member at the locus of said meniscus having a magnitude which corresponds to a predetermined ventilatory flow rate, whereby peak ventilatory flow rate is indicated by the identity of said openings from which such meniscus is dislodged.

2. An indicator according to claim 1 wherein said series of openings is arranged along the length of said elongated tubular member.

3. An indicator according to claim 2 wherein said series of openings is arranged in a straight line parallel to the longitudinal axis of said elongated tubular member.

4. A peak ventilatory flow rate indicator comprising an elongated tubular member having both ends open, one end serving as a mouthpiece, a constricting member for resisting air flow when air is discharged into said mouthpiece thereby to produce across the wall of said tubular member a pressure drop having a magnitude functionally related to ventilatory flow rate, and a series of openings through the wall of said tubular member for retaining thereacross a meniscus of a selected liquid, said constricting member being situated at the side of said series of openings opposite said one end, each of said openings being of a distinctive size so that such meniscus thereacross is dislodged by a pressure drop across the wall of said tubular member having a magnitude which corresponds to a predetermined ventilatory flow rate, whereby peak ventilatory flow rate is indicated by the identity of said openings from which such meniscus is dislodged, further comprising at least one removable adapter for increasing resistance to air flow through said tubular member to a level above that provided by said constricting member.

5. A peak ventilatory flow rate indicator comprising an elongated tubular member having both ends open, one end serving as a mouthpiece; an inwardly projecting annular flange forming a constriction thereby to produce across the wall of said member a pressure drop having a magnitude functionally related to ventilatory flow rate; a series of openings through the wall of said member for retaining thereacross a meniscus of a selected liquid, said flange being at the side of said series of openings opposite said one end, each of said openings being of a distinctive size so that such meniscus thereacross is dislodged by a pressure drop across the wall of said member having a magnitude which corresponds to a predetermined ventilatory flow rate, whereby peak ventilatory flow rate is indicated by the identity of said openings from which such meniscus is dislodged; and removable adapter means configured to mate with the end of said tubular member opposite said one end and having a second inwardly projecting annular flange for forming a second constriction smaller than the first said constriction.

6. The indicator of claim 5 further comprising two or more removable adapters, each configured to mate with the end of said tubular member opposite said one end, each having an inwardly projecting annular flange for forming a constriction smaller than the first said constriction and of a size different than the constriction in any other such adapter.

7. A peak ventilatory flow indicator comprising an elongated tubular member having both ends open, one end serving as a mouthpiece, means for constricting said member and resisting the passage of air therethrough when air is discharged into said mouthpiece thereby to produce across the wall of said member a pressure drop having a magnitude functionally related to ventilatory flow rate, and means intermediate said one end and said constricting means forming a series of openings through a portion of the wall of said member for retaining thereacross a meniscus of a selected liquid, each of said openings being of a distinctive size so that such meniscus thereacross is dislodged by a pressure drop across the wall of said member having a magnitude which corresponds to a predetermined ventilatory flow rate, whereby peak ventilatory flow rate is indicated by the identity of said openings from which such meniscus is dislodged.

8. An indicator according to claim 7 wherein the air passage formed by said elongated tubular member is characterized by minimal resistance to air flow and substantially all resistance to air flow is produced by said constricting means.

9. An indicator according to claim 7 wherein the portion of said elongated tubular member intermediate said one end and said constricting means is of substantially uniform size and configuration along at least the portion of its length bearing said series of openings.

10. The indicator according to claim 7 wherein said constricting means comprises an inwardly projecting annular flange.

11. A peak ventilatory flow rate indicator comprising an elongated tubular member having both ends open, one end serving as a mouthpiece, said member being constricted to resist air flow when air is discharged into said mouthpiece thereby to produce across the wall of said member a pressure drop having a magnitude functionally related to ventilatory flow rate, and a series of openings through the wall of said member for retaining thereacross a meniscus of a selected liquid, said openings being arranged along the length of said member in a line parallel to the longitudinal axis thereof with the largest opening at one end of said line and the others in descending order of size, each of said openings being of a size predetermined so that such meniscus thereacross is dislodged by a pressure drop across the wall of said member having a magnitude which corresponds to a predetermined ventilatory flow rate, whereby peak ventilatory flow rate is indicated by the identity of said openings from which such meniscus is dislodged.

12. An indicator according to claim 11 wherein said largest opening is closest to said mouthpiece.

* * * * *